US012700179B2

(12) United States Patent (10) Patent No.: US 12,700,179 B2

Schreckenberg et al. (45) Date of Patent: Aug. 4, 2026

(54) EXTENDED REALITY-BASED USER INTERFACE ADD-ON, SYSTEM AND METHOD FOR REVIEWING 3D OR 4D MEDICAL IMAGE DATA

(71) Applicant: KONINKLIJKE PHILIPS N.V., Eindhoven (NL)

(72) Inventors: Marcus Schreckenberg, Freising (DE); Michael Blankenhagen, Roehrmoos (DE); Niklas Domenic Maria Hitschrich, Germany (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 256 days.

(21) Appl. No.: 18/010,057

(22) PCT Filed: Jun. 16, 2021

(86) PCT No.: PCT/EP2021/066205

§ 371 (c)(1),
(2) Date: Dec. 13, 2022

(87) PCT Pub. No.: WO2021/259724

PCT Pub. Date: Dec. 30, 2021

(65) Prior Publication Data

US 2023/0230321 A1 Jul. 20, 2023

(30) Foreign Application Priority Data

Jun. 23, 2020 (EP) ..................................... 20181714

(51) Int. Cl.
G06T 17/20 (2006.01)
G06F 3/0346 (2013.01)
(Continued)

(52) U.S. Cl.
CPC ............ G06T 17/20 (2013.01); G06F 3/0346 (2013.01); G06T 7/0012 (2013.01); G06T 7/10 (2017.01);
(Continued)

(58) Field of Classification Search
None
See application file for complete search history.

(56) References Cited

U.S. PATENT DOCUMENTS

| | | | |
|---|---|---|---|
| 10,769,797 B2 * | 9/2020 | Budagavi | G06F 3/011 |
| 2018/0075654 A1 * | 3/2018 | Vembar | G06T 7/70 |

(Continued)

FOREIGN PATENT DOCUMENTS

| | | | | |
|---|---|---|---|---|
| CN | 107688348 A | * | 2/2018 | G05D 1/0808 |
| JP | 2020000863 A | | 1/2020 | |

(Continued)

OTHER PUBLICATIONS

International Search Report and Written Opinion for PCT/EP2021/066205; Mailing date: Sep. 1, 2021, 15 pages.

(Continued)

*Primary Examiner* — Saptarshi Mazumder

(57) ABSTRACT

The invention relates to a system (1) for reviewing 3D or 4D medical image data (2), the system (1) comprising (a) a medical review application (MRA) (4) comprising a processing module (6) configured to process a 3D or 4D dataset (2) to generate 3D content (8), and a 2D user interface (16); wherein the 2D user interface (16) is configured to display the 3D content (8) and to allow a user (30) to generate user input (18) commands; (b) an extended reality (XR)-based user interface add-on (XRA) (100); and (c) a data exchange channel (10), the data exchange channel (10) being configured to interface the processing module (6) with the XRA (100); wherein the XRA (100) is configured to interpret and (Continued)

process the 3D content (8) and convert it to XR content displayable to the user (30) in an XR environment (48); wherein the XR environment (48) is configured to allow a user to generate user input (18) events, and the XRA (100) is configured to process the user input (18) events and convert them to user input (18) commands readable by the MRA (4). The invention also relates to an extended reality-based user interface add-on (100), a related method for analysing a 3D or 4D dataset (2), and a related computer program.

18 Claims, 6 Drawing Sheets

(51) Int. Cl.
    G06T 7/00         (2017.01)
    G06T 7/10         (2017.01)
    G16H 30/20        (2018.01)
(52) U.S. Cl.
    CPC ...  G16H 30/20 (2018.01); G06T 2207/10132 (2013.01); G06T 2207/30048 (2013.01)

(56) References Cited

U.S. PATENT DOCUMENTS

| 2018/0189958 | A1 | 7/2018 | Budagavi et al. |
| 2018/0200018 | A1 | 7/2018 | Silva et al. |
| 2019/0356894 | A1* | 11/2019 | Oh ................. H04N 21/234345 |
| 2019/0365498 | A1 | 12/2019 | Gibby et al. |
| 2021/0347910 | A1 | 11/2021 | Nakada et al. |

FOREIGN PATENT DOCUMENTS

| JP | 2020029711 | A | 2/2020 |
| WO | 2017072616 | A1 | 5/2017 |
| WO | 2017165301 | A1 | 9/2017 |
| WO | 2019106014 | A1 | 6/2019 |
| WO | 2019185601 | A1 | 10/2019 |
| WO | 2020026223 | A1 | 2/2020 |

OTHER PUBLICATIONS

Mandalika, V.B.H. et al., "A Hybrid 2D/3D User Interface for Radiological Diagnosis", J Digit Imaging, 2018, vol. 31, pp. 56-73.
Bornik, A. et al., "A Hybrid User Interface for Manipulation of Volumetric Medical Data", IEEE Symposium on 3D User Interfaces, 2006, pp. 29-36.
Sorensen, T.S. et al., "A new virtual reality approach for planning of cardiac interventions", Artificial Intelligence in Medicine, 2001, vol. 22, pp. 193-214.
Rey, A. et al., "A Novel Visualizer of Medical Images by Integrating an Extensible Plugin Framework", Ambient Assisted Living and Home Care, 2012, pp. 41-48.
Kuester, F. et al., "VirtualExplorer: A Plugin-Based Virtual Reality Framework", Proceedings of SPIE—The International Society for Optical Engineering, 2001, vol. 4297, pp. 436-442.
Anonymous, "Plug-in (Computing)", Wikipedia, 2016, 3 pages.
Febretti, A. et al., "The OmegaDesk: Towards A Hybrid 2D & 3D Work Desk", 7th International Symposium on Visual Computing (ISVC11), 2011, 13 pages.

* cited by examiner

EXTENDED REALITY-BASED USER INTERFACE ADD-ON, SYSTEM AND METHOD FOR REVIEWING 3D OR 4D MEDICAL IMAGE DATA

CROSS-REFERENCE TO PRIOR APPLICATIONS

This application is the U.S. National Phase application under 35 U.S.C. § 371 of International Application No. PCT/EP2021/066205, filed on Jun. 16, 2021, which claims the benefit of European Patent Application No. 20181714.5, filed on Jun. 23, 2020. These applications are hereby incorporated by reference herein.

FIELD OF THE INVENTION

The invention relates to a system for reviewing 3D or 4D medical image data, an extended reality-based user interface add-on, a method for analysing a 3D or 4D dataset, and a related computer program.

BACKGROUND OF THE INVENTION

For the visualisation of internal structures of a human or animal body, in particular of organs and tissues, medical imaging modalities, such as X-ray computed tomography (CT), magnetic resonance imaging (MRI) and ultrasound, are generally used to acquire two-dimensional (2D), three-dimensional (3D) or four-dimensional (4D) images (the fourth dimension being time) of the interior of the body. These medical images play an important role in the planning of surgical interventions. Especially in interventions in which a medical implant is implanted, for example an artificial heart valve, a comprehensive presentation of the anatomy allowing the most accurate planning possible is crucial for the success of the treatment.

3D image data sets may be either acquired directly, or they may be produced by scanning a number of adjacent 2D image slices, usually in a regular pattern, and combining them, e.g. by a computer, into a volumetric grid. Each volume element (voxel) of the 3D image is assigned the grey-scale value of the pixel in the respective 2D image slice, which represents the region around the voxel coordinates.

From a 3D image, 2D image planes can be generated in any orientation by interpolating the voxel/pixel values closest to the desired 2D image plane. This process is called Multi Planar Reconstruction (MPR) and is often used to visualise a 3D image dataset.

In order to enable physicians to examine 3D images of the internal structures of a body on a two-dimensional screen, a number of techniques have been developed. Volume rendering, for example, is a set of techniques used to display a 2D projection of a 3D discretely sampled dataset, such as a medical 3D image. To render a 2D projection of the 3D dataset, one needs to define a camera position relative to the image volume. One also needs to define properties of each voxel, such as opacity and colour. This is usually defined using an RGBA (red, green blue, alpha) transfer function that defines the RGBA value for every possible voxel value. In order to simplify the rendering process, often a threshold is used, wherein voxels having a value below the threshold are treated as having a value of zero, in order not to clutter the view onto the important structures. Different techniques, such as volume ray casting, splatting, shear warp or texture-based volume rendering may be used.

While in many cases the image data sets are three-dimensional in nature, the analysis of clinical data and surgical planning is conventionally done on two-dimensional screens. Although there are already very sophisticated software solutions available for most clinical applications, the navigation within 3D datasets is still mostly done by manually shifting, tilting and rotating MPR planes within a volume, or rotating flat 2D representations of 3D volume-rendered models. Generating a conceptual mental 3D model from these MPR planes or volume renderings planes not only requires a lot of experience and good spatial imagination, but always carries the risk of wrong clinical decisions due to misinterpreting depth information or anatomical correlations. Advanced colouring and shading is often used to generate and support the impression of depth on the two-dimensional screen. Furthermore, 2D input devices, such as a computer mouse, that are conventionally used, are optimized for the manipulation of 2D objects. Thus, working on 3D objects via MPR planes is not only unintuitive in some cases, especially for people new to the field, but can often also be quite time consuming.

An approach to improve workflows concerning medical 3D image datasets is the use of 3D representations such as virtual reality (VR) or 3D screens. The application of such technologies has become more and more feasible during recent years. For the first time, the technical developments in the field of virtual reality enable end-customers to buy affordable, off-the-shelf hardware and software. Examples of this are the well-received HTC Vive or the Oculus Rift VR headset, which have been available since 2016 and have launched a new era in the gaming and entertainment industry. Current developments will make this technology (especially augmented reality) available to the broad public in the next years (Apple AR Kit, Apple AR glasses in 2020, Oculus Quest, Vive Focus etc.)

The advantages of these VR headsets are the (partial or complete) immersion in a virtual environment and the real 3D representation of 3D content. In addition, the highly intuitive control via tracked hand controllers allows a very natural interaction with virtual objects (e.g. grabbing, rotating).

As neither standard 2D screens nor an VR environment are optimal for the entire medical workflow, virtual reality interfaces have been used in combination with 2D interfaces in order to benefit from the advantages of both systems. For example, A. Bornik et al. have proposed such a combination in "A Hybrid User Interface for Manipulation of Volumetric Medical Data," 3D User Interfaces (3DUI'06), Alexandria, VA, USA, 2006, pp. 29-36, doi: 10.1109/VR.2006.8. Here the user can switch between a stereoscopic screen using shutter glasses and the 2D screen of a tablet PC, wherein both applications share a large portion of their programmed code. A similar approach is proposed by V. Mandalika et al. in "A Hybrid 2D/3D User Interface for Radiological Diagnosis". J Digit Imaging 31, 56-73 (2018), doi: 10.1007/s10278-017-0002-6, where a user can switch between a 2D display using mouse and keyboard and a 3D zSpace display using a stylus pen for input. Sorensen et al. propose in "A new virtual reality approach for planning of cardiac interventions", Artificial Intelligence in Medicine 22, 2001, 193-214 an approach to 3D visualization of MR data It is based on a tool for interactive, real-time visualization of 3D cardiac MR data sets in the form of 3D heart models displayed on virtual reality equipment.

However, implementing such combinations of virtual reality and 2D interfaces is computationally complex, and requires special equipment, which is likely to be a problem for many medical facilities that have to work on a limited budget and have limited space available. Replacing existing equipment with these new options or providing space and money for additional equipment may often not be an option.

OBJECT OF THE INVENTION

It is, therefore, an object of the invention to provide a system and a related extended reality-based user interface add-on, method and computer program that facilitates and optimizes the navigation within and analysis of 3D datasets, while at the same time minimizing additional expenses associated with such a new system and maintaining the benefits of conventional systems.

SUMMARY OF THE INVENTION

This object is met or exceeded by a system for reviewing 3D or 4D medical image data, an extended reality-based user interface add-on, a method for analysing a 3D or 4D dataset and a computer program. Advantageous embodiments are also described. Any features, advantages or alternative embodiments described herein in relation to the claimed system are also applicable to the other claim categories, in particular the claimed extended reality-based user interface add-on, the method, and the computer program and vice versa.

According to the invention, a system for reviewing 3D or 4D medical image data is provided, the system comprising (a) a medical review application comprising a processing module configured to process a 3D or 4D dataset to generate 3D content, and a 2D user interface, wherein the 2D user interface is configured to display the 3D content generated by the processing module and to allow a user to generate user input commands;

(b) an extended reality (XR)-based user interface add-on;

(c) a data exchange channel operatively coupled to the processing module, the data exchange channel being configured to interface the processing module with the extended reality (XR)-based user interface add-on;

wherein the data exchange channel is adapted to direct the 3D content generated by the processing module to the extended reality-based user interface add-on, and wherein the extended reality-based user interface add-on is configured to interpret and process the 3D content and convert it to XR content displayable to the user in an extended reality environment;

wherein the extended reality environment is configured to allow a user to generate user input events, and the extended reality-based user interface add-on (100) is configured to process the user input events and convert them to user input commands readable by the medical review application; and wherein the data exchange channel is adapted to direct user input commands from the extended reality-based user interface add-on to the medical review application.

The advantage of the inventive system is that the extended reality (XR)-based user interface add-on is comparatively independent of and decoupled from the medical review application, which may be an already existing software solution for reviewing, in particular displaying and analysing, 3D medical images, such as for example one of the advanced TOMTEC® 4D clinical application packages (CAPs), such as 4D LV Analysis, 4D RV Function, 4D MV Assessment or 4D Cardio-View. If at all, only slight modifications have to be made to these powerful and well-established medical software products, in order to allow the exchange of data, e.g. the communication of volume data (3D or 4D datasets), graphical objects, coordinate systems and user interactions, with the extended reality (XR)-based user interface add-on. In particular, the medical review application does not need to be able to directly drive or control XR hardware, such as VR goggles, since this functionality is situated in the XR-based user interface add-on. The XR-based user interface add-on may be configured to allow the application of various different XR hardware types, or there may be several XR-based user interface add-ons available, each for a different XR hardware type. Furthermore, the XR-based user interface add-on can be used for different medical review applications, which again simplifies implementation. Therefore, the system of the invention allows XR-interaction for dedicated workflows of an existing medical product (medical review application) without complete re-implementation. Instead, the XR-based user interface add-on provides a remote control and view add-on that provides all functionality for various XR workflows, yet without any re-implementation of the business logic of the original medical product. By using the system of the invention, the user can change between 2D and XR at any time and experiences a seamless integration of the two different user interfaces. The XR content is always in perfect sync with the medical review application. Accordingly, workflows can be realised in which some measurements or other workflow steps are carried out using the 2D user interface, and others, that require better spatial overview of the image, may be carried out using the XR environment.

The system of the invention is preferably implemented as a software product comprising a medical review application and an extended reality-based user interface add-on, connected by a data exchange channel. Such software may be installed on any computer or other digital processing device. The system may also be embodied in hardware, in particular a computer having a processing unit, a data storage and devices to allow user input and output, as explained in more detail below.

The 3D or 4D medical image data may be any 3D or 4D image datasets generated by means of a medical imaging modality, such as CT, MRI or ultrasound. It is also possible that the system can process several 3D or 4D datasets at the same time. Processing the 3D or 4D dataset may in particular comprise a rendering of the 3D or 4D dataset into 2D or 3D image or video data, 3D image or video data may in particular be two sets of 2D image or video data adapted to be provided for a 3D stereoscopic view, as used by the extended-reality user interface. The 3D or 4D medical image data preferably depicts a part of the human or animal body, such as an internal organ, a limb or part thereof, a head, brain, fetus etc. The system of the invention is particularly useful in reviewing 3D or 4D medical image data of the moving human heart, in particular 4D image data, i.e. a time series of 3D image datasets acquired over at least one heartbeat. Images of this kind may be acquired with transesophageal ultrasound probes and are often used to analyse the function of the heart, in particular the pumping action of the ventricles, as well as the functioning of the heart valves, and for planning heart surgeries, such as replacing a heart valve with an implant. In the planning of such surgical interventions, the best possible visualization of the complex and dynamic valve structure is essential.

The medical review application may also be referred to as 3D software product, since it is designed to review 3D or 4D medical image data, wherein reviewing comprises e.g. visualizing the images and the anatomical structures contained therein, allowing the user to navigate through these images, for example by manually shifting and tilting MPR planes through the volume, providing 2D representations of the 3D or 4D dataset by techniques such as volume rendering or surface rendering, and analysing the dataset for example by fitting 3D models to the anatomical structures. The medical review application may also allow a user to take measurements within the 3D or 4D dataset, or checking the goodness of fit of a model. All of these functionalities may be part of the medical review application, which may for example have the functionalities of the TOMTEC® CAPs mentioned above.

The medical review application comprises a processing module which is configured to process the 3D or 4D dataset to generate 3D content, 3D content preferably is data having spatial coordinates, in particular 3D coordinates in the image space of the 3D or 4D image dataset. Thus, the 3D content may comprise 3D image data (volume data), graphical objects, such as a mesh representing a model or graphical primitives, or an MPR plane, which generally consists of a 2D image, referred to as the MPR texture, and the position and orientation of the MPR plane in 3D image space. The processing may comprise calculations performed upon the 3D or 4D dataset, which generate either a modified 3D or 4D dataset, a visualization of the 3D or 4D dataset (such as volume rendering) or may involve analysing the 3D or 4D dataset, such as fitting a model to anatomical structures, performing measurements within the dataset, calculating an MPR texture etc. The processing of the 3D or 4D dataset may be based on user input commands, for example relating to the shifting, rotating or tilting of an MPR plane, the correction of a model, or 3D mouse positions indicating the spatial coordinates of measurement points or anatomical landmarks set by a user. The 3D content may be passed from the processing module to the 2D user interface and/or the XR-based user-interface add-on in the form of 2D or 3D (i.e. stereoscopic) image or video data, obtained for example by rendering methods from the 3D or 4D dataset, or by calculating an MPR plane through the 3D or 4D dataset.

Furthermore, the medical review application also comprises a 2D user interface, which is configured to display the 3D content generated by the processing module and to allow a user to generate user input commands. The 2D user interface is preferably a non-XR-based user interface, meaning it does not involve representations in extended or virtual reality. Preferably, the 2D user interface comprises a window (also referred to as diagnostic region) for displaying images, as well as a graphical user interface (GUI) which enables the user to interact with the application. The GUI usually comprises various buttons, sliders, and/or numerical input fields, which may be either on a screen to be operated on by a cursor, or may be implemented in a separate user input device. The 2D user interface is usually already available as part of the medical review application and allows a user to generate user input commands by interacting with the GUI and/or by marking specific points, lines or regions on the displayed image in the diagnostic region.

In addition to this stand-alone medical review application, the system of the invention comprises a data exchange channel operatively coupled to the processing module of the medical review application, which is configured to interface the processing module with an extended reality-based user interface, which is preferably operatively coupled to the data exchange channel. Herein, the term "Extended Reality" (XR) is meant to cover all of virtual reality (VR, complete immersion in a virtual environment), augmented reality (AR, the user sees the real world around him with virtual objects placed therein), and mixed reality (MR, virtual objects interact with real objects, e.g. real objects may obstruct the view on virtual objects). Thus, an XR environment is one that allows a user to view the 3D content stereoscopically, i.e. each eye sees a slightly different image, resulting in a "real" 3D representation of 3D content, which is then termed "XR content". Accordingly, orientation within a 3D dataset is much more intuitive and simpler when using the XR-based user interface add-on, also referred to as XRA. Moreover, the XR-based user interface add-on may allow a user to interact with virtual objects, in particular the displayed XR content, i.e. by grabbing and rotating using tracked hand controllers. This is a very intuitive way of interaction.

Accordingly, user input events may be generated by the user within the extended reality environment, such as deforming a 3D mesh, which e.g. represents a model of an anatomical structure, making annotations or placing a graphical object representing e.g. a device, such as an implant. Such user input events may be generated by moving tracked hand controllers (XR controller) and at the same time actuating a button on the controller. Accordingly, an XR controller is like a 3D mouse. In the XR environment. i.e. in the scene that is presented to the user when using the XR-based user interface add-on, the user will see the displayed XR content, and possibly also user interface elements (UI elements), which he can actuate using the XR controller to for example change the settings concerning the display of the XR content such as contrast or brightness, or to indicate the start of a certain step in the workflow, e.g. a certain measurement or interaction with a virtual object.

The role of the XR-based user interface add-on is to process such user input events, if the user chooses to generate any, to convert them to user input commands, which are readable by the processing module, and to direct them through the data exchange channel to the processing module. For example, the XR-based user interface add-on may process a movement of an XR controller from a first 3D point to a second 3D point into the user input command "move currently grabbed object from first point to second point" and direct this command to the processing module.

The 3D content generated by the processing module will be directed to the XR-based user interface add-on through the data exchange channel. Preferably, this will be done at any time while the processing module is active, i.e. the data exchange channel is adapted to direct the 3D content generated at any time by the processing module to the XR-based user interface add-on. It may also be done only during a connection between the processing module and the XR-based user interface add-on, i.e. w % ben the XRA is active. The latter is configured to interpret and process the 3D content and convert it to XR content displayable to the user in the XR environment. This conversion will e.g. comprise the generation of the two slightly different views of the 3D content to be presented to each eye for stereoscopic viewing. The conversion may in particular comprise the adaptation of the 3D content to the momentary head position and/or viewing perspective, as detected by the VR hardware used, for example by applying perspective distortion. Thereby, the 3D content is converted to XR content.

The data exchange channel accordingly allows the exchange of various kinds of data and information between the medical review application (MRA) and the extended reality-based user interface add-on (XRA). One could say that this exchange allows remote control of the otherwise isolated 3D software product (MRA) by an external application (XRA). Therein, 3D content, in particular pre-defined 3D content such as a 3D mesh generated by the processing module e.g. through segmentation of the 3D or 4D medical image data, or 3D measurements, are to be transferred. Further, preferably user interface elements (such as the number of a current frame, settings concerning the display of the 3D content, etc.) may be synchronized between the two applications.

Conversely to the prior art, in the present invention the more complex calculations, such as the generation of an MPR plane (MPR texture), generation of a measurement, segmentation, generation of a model of an anatomical structure, and deforming such a model, are all carried out by the MRA, while the XRA will have as few tasks as possible, and just as many as necessary in order to support a clinical workflow step. Such workflow step may for example be the review and modification of a model represented by a graphical object such as a mesh, wherein the model might be a mitral valve segmentation, by means of the stereoscopic XR view and the 18 degrees of freedom given by an XR headset and two XR controllers. Therein, the XRA will allow a user to generate user input, for example "take this point in the model and move it one cm to the right", but the actual modification of the model will be made by the MRA. The amended graphical object representing the model will be transferred back to the XRA. Because the XRA follows simple instructions, in particular to display certain 3D content, such as " . . . display object 1 at position 1 and object 2 at position 2", the XRA is independent of the MRA and may be used with many different MRAs.

The data exchange channel transfers data between the MRA and the XRA. When information is directed from the MRA to the XRA, the XRA processes the information to allow its display in the XR environment. Information sent from the XRA to the MRA, such as user input commands, may be processed and displayed by the MRA.

According to an embodiment, the MRA comprises a data interface for the XRA, wherein the data interface is operatively coupled to the data exchange channel, and is configured to allow the exchange of simplified and standardized operating actions and data between the MRA and the XRA. Accordingly, the data interface is placed between the back end (MRA) and the front end (XRA) of the system according to the invention, and defines the type of data that can be exchanged between the two. For example, it allows the exchange of the simplified and standardized operating actions. Operating actions may, for example, comprise a 3D mouse position and/or user input commands.

In an embodiment, at least a part of the data interface is message-based, and the messages are defined through user interface elements (UI elements). Preferably, at least some of the UI elements may be modified by the user by actuating corresponding buttons or sliders on the GUI and possibly in the XR environment, other UI elements may be changed by other user input, such as mouse/controller events. Messages exchanged may refer to a unique UI element defined by its unique ID (UID). The UI elements have also a distinct type, defining which kind of value they transport. Such types may for example be string, Boolean, integer values, double values, etc. Thus, an exchanged UI element can have one of the following events attached to the message:

UIevent_Value_Changed: This event is sent if the value of the parameter the UI element is representing has changed. All UI elements may send this event. According to the invention, the direction of the communication may be in both directions, allowing synchronization of UI elements between MRA and XRA.

UIevent_Enable_Changed: By sending this event, the MRA tells the XRA that a certain parameter is enabled or disabled. If a UI element is not enabled, no UIevent_Value_Changed event will be sent or accepted. This type of message is only sent to the XRA.

UIevent_Range_Changed: This event indicates that the valid range of a value has changed. This type of message is only sent to the XRA and only valid for UI elements that are in a defined range.

This embodiment is merely an illustration on how the data exchange between the XRA and the MRA may be implemented. It shows that MRA and XRA may be built independently, only a list of UI elements with the description of their purpose and usage, as well as possible 3D content, have to be defined.

Regarding the 3D content to be processed by the XRA, it is possible that the processing module will perform all processing of the 3D or 4D dataset, so that the 3D or 4D dataset itself is not transferred to the XRA, but only respective volume renderings or MPR textures, together with their 3D position and orientation, as well as other graphical objects such as meshes or graphical primitives and annotations. Alternatively, the 3D or 4D dataset itself may be transferred to the XRA, which in this embodiment is able to process it in order to generate stereoscopic renderings, in particular volume renderings. The XRA may also receive a data-reduced, simplified or data-compressed version of the 3D or 4D dataset.

According to an embodiment, the data interface is adapted to continuously synchronize corresponding user interface elements (UI elements) between the XRA and the MRA through the data exchange channel, wherein the corresponding user interface elements comprise at least one of the value of the user interface element, and identifier of a selected frame of a 4D dataset, settings concerning the display of the 3D and/or XR content, and/or a 3D mouse position. UI elements accordingly, may be any vector or parameter that relates to the display of the 3D and/or XR content. In some embodiments, also the position of a 3D/XR cursor may be continuously synchronized between MRA and XRA. In other embodiments, such cursor position is not continuously synchronized. However, the user input events in the XR environment generated with XR controllers, which incorporate a 3D mouse position, are transferred from the XRA to the MRA when necessary, for example when a measurement is to be initiated or a segmentation, model or other graphical object is to be adapted. In some embodiments, the settings concerning the display of the 3D and/or XR content as well as the current frame of a sequence of 3D images (4D datasets) are continuously synchronized between MRA and XRA in both directions, so that the 3D content displayed to the user in the 2D user interface is displayed in a comparable manner as XR content in the XR environment. The settings concerning the display of 3D/XR content may for example be brightness and contrast, as well as parameters relating to a volume rendering of the 3D/XR content, such as threshold and opacity.

According to a preferred embodiment, the UI elements are synchronized between MRA and XRA, wherein the MRA nevertheless is responsible for maintaining the values for the UI elements. This may imply that certain UI elements have pre-defined maximum or minimum values which are unknown to the XRA. Thus, the XRA may communicate a user input command that a UI element be increased. However, if the UI element has already reached its maximum value, the MRA will answer by re-sending the old value for the UI element. Thus, the synchronization of UI elements is managed by the medical review application, wherein the XRA can only communicate its wishes to change the UI elements, but the medical review application decides whether these changes are made or not.

Accordingly, in an embodiment, the XRA is stateless, in that it does not have a memory of user input commands transferred to the processing module through the data exchange channel. Also by this measure, the XRA can be kept slim with as little internal intelligence as possible. In preferred embodiments, the XRA is only able to transfer user input commands and to receive commands regarding the display of 3D content from the MRA, and preferably has no further functionality. In an embodiment where the XRA is stateless, it can easily be plugged-on to various medical review applications, and require little or no memory/buffer.

According to a preferred embodiment, a stream of data comprising 3D content and optionally user input commands are exchanged through the data exchange channel by means of a data connection. Preferably, this may be a standard data connection. For example, the communication between MRA and XRA can be via a TCP/IP socket connection. For example, messages may be exchanged as strings with a defined format like "<UID>|<event>|<value>". For example, the message "threshold tissue|value changed|125" sets the threshold for volume rendering to 125. In this setup, the MRA and the XRA could run in different processes, such as on different processing units. Another way to communicate is via a DLL interface. The application can be integrated into a C++ DLL. This DLL provides a function "set UI element" (UID event, value) for the communication between XRA and MRA. In this setup, MRA and XRA are running in the same process, but in separated threads.

According to an embodiment, the 3D content generated by the processing module may comprise a rendering of the 3D or 4D dataset, wherein the extended reality-based user interface add-on is configured to adapt, in particular distort in perspective, the rendered 3D content based on at least some of the user input and/or a user's current viewing perspective. The rendered 3D content is in particular image or video content created via the rendering of the 3D or 4D dataset. In particular, the extended reality-based user interface add-on may be configured to adapt the viewing perspective more quickly than the rate of a data stream of rendered image or video data from the medical review application to the extended reality-based user interface add-on. E.g., the data stream may be updated ca. 10 times per second, while the XR-based user interface add-on may be configured to update the viewing perspective 30 to 120 times per second, and thereby provide a realistic XR environment to the user, which for example reacts quickly to head movements by the user wearing a VR headset.

According to an embodiment, responsive to a "switch user interface" command generated by a currently-active user interface among the XRA and the 2D user interface, the processing module is adapted to stop responding to user input commands from said user interface and to start responding to user input commands from the other user interface. Thereby, the XR environment may be seamlessly integrated into the medical review application, without imposing any additional software on the user, except the XRA. During a routine 2D workflow executed on the 2D user interface, the user can thus give a user input command, e.g. click one button "view in XR", and put on his headset to enter the 3-dimensional XR environment. e.g. a VR space. He can then execute a part of the workflow in XR, preferably a part that is cumbersome to do in 2D. Afterwards, he may put down the headset and can instantly continue to work on his 2D workflow on the 2D user interface.

According to an embodiment, the 3D content generated by the processing module comprises at least one of the 3D or 4D dataset itself, an updated or data-compressed version of the 3D or 4D dataset, a rendering of the 3D or 4D dataset, a particular frame of a 4D dataset, an MPR texture generated from the 3D or 4D dataset, a graphical primitive, a 3D or 4D model of an object, such as an anatomical structure, a mesh, a text of an annotation, and/or a number indicating a measurement. Thus, the processing module may transfer volume data, such as the 3D or 4D dataset or an updated version thereof, for example a version that has been segmented, or cropped to cut off the non-relevant tissue, to the XRA. The XRA will then process the volume data to generate XR content, for example by rendering the same, such as volume rendering or surface rendering, wherein the rendering will result in two slightly different views for each eye for stereoscopic viewing. In another embodiment, the processing module will perform the rendering of the volume data itself and transfer the rendered views to the XRA. The processing module may also transfer a particular frame of a 4D dataset, i.e. one of a time sequence of 3D datasets. In another embodiment, the processing module will once transfer the complete 4D dataset, which is, in this embodiment, buffered by the XRA during the complete review session. The processing module in this embodiment need not transfer a particular frame, but only the identifier or number of the respective current frame. Another type of 3D content may be a 2D image generated from the 3D or 4D dataset by multiplanar reconstruction, a so-called MPR texture, together with its position and orientation. The XRA may then generate the MPR plane in the XR environment at the correct position and orientation.

Another type of 3D content is a 3D or 4D model of an object, typically of an anatomical structure, such as a heart valve or a heart chamber, or the model of an implant, for example a model of an artificial heart valve. The model may be in 4D, i.e. it may change over time, for example over one heartbeat. A model is preferably a simplified, parametric representation of the modelled object. The model will typically be a surface model, i.e. it is constructed of one or several, possibly moving, surfaces. In a preferred embodiment, the 3D or 4D model of an anatomical structure is represented by a mesh, i.e. it is defined by a set of points in space, which span a triangular mesh. An important application of the invention is also the displaying of implants as a 3D or 4D model. By allowing the user to move around the 3D or 4D model of an implant in the XR environment, while at the same time displaying a volume rendering of the 3D or 4D dataset, e.g. the heart, the user is able to very efficiently and correctly place the implant and plan the surgery. Further, 3D content may also be an annotation, or rather the text thereof, as well as its 3D position, allowing the XRA to display the annotation text at its correct position in space in the XR environment. Similarly, also a number indicating a measurement may be transferred. Further, 3D content may be a landmark position in the 3D image space. Another type of 3D content which may be transferred may be termed graphical primitive, which may be any standardized graphical object, such as a text window, a line, a point, or a graphical object such as a triangle, a number of triangles, a sphere, etc. Also, diverse dynamic graphical primitives may be transferred, e.g. to display (textured) surface models, measurements and annotations/landmarks. In an embodiment, the XRA is able to buffer such graphical primitives in order to achieve a smooth dynamic display.

In an embodiment, during establishment of a connection between the processing module and the XRA, the processing module is adapted to transfer a temporal and spatial reference system and at least one of the 3D or 4D dataset, a user interface element and optionally configuration settings to the XRA. This may be done through the data interface of the MRA. This will serve to initialize the XRA and enable it to communicate smoothly with the processing module. The configuration settings can either be deployed together with the XRA, or can be transferred by the processing module during establishment of a connection, e.g. at the beginning of a review session. This is especially preferably if the XRA is potentially used for more than one medical review application. The configuration settings to be transferred during establishment of a connection may comprise a unique application identifier (application name and a version of the medical review application), special start options/flags, and/ or exchange configuration, such as IP address, port and exchange folders. The configuration settings may also comprise protocol configuration (protocol version, allowed types of commands), configuration settings of the UI elements (which buttons and menus) and/or style for data objects (line width, line colour, etc). Accordingly, fundamental data may be transferred when starting a session (establishment of a connection), which provides a reference system for the further data exchange between MRA and XRA during a session. The temporal and spatial reference system may comprise a common temporal reference system for the exchange between MRA and that allows to convert between frames and times. It serves as a reference system to define phase loops and time stamps. A spatial reference coordinate system is further exchanged that allows to convert between mm and pixel coordinates in image space. It serves as a spatial reference system e.g. to position XR objects in relation to the 3D volume. Moreover, the 3D or 4D dataset may be passed at the start of the session and, in an embodiment, is treated as invariable during a session.

According to an embodiment, the extended reality-based user interface add-on (XRA) is adapted to transfer at least one of a 3D mouse position, a position and orientation of an MPR plane, a screenshot, and/or a modified value of a user interface element, through the data exchange channel to the processing module, during a connection between the processing module and the XRA. Thereby, the XRA can act as a "remote control" to the medical review application, like a 3D mouse. Accordingly, user input events such as a click on a XR controller at a certain position in space, i.e. a 3D mouse position, may be transferred to the MRA as a user input command. Such a command may for example indicate that a 3D model is adapted, by grabbing a point on the displayed mesh and dragging it to one side. However, the XRA does not maintain the model itself, but only transfers the 3D mouse positions and respective user interactions, e.g. the 3D position of a first click, and a 3D position of a second click, and the information that these user input events relate to the modification of the 3D model. The processing module will translate these user input commands into a modification of the model. Similarly, the XRA may transfer the desired position and orientation of an MPR plane in the form of user input commands. However, the processing module will do the calculations to calculate a new MPR texture, relating to the transferred position and orientation. The new MPR texture will be transferred back to the XRA. In an embodiment, also a screenshot generated in the XR environment may be transferred from the XRA to the processing module, in order to document an executed workflow step. Moreover, the XRA may transfer UI elements, or modified values thereof, as described above. In preferred embodiments, the UI elements are continuously synchronized between the MRA and the XRA. This kind of data may be termed transient data, as it is data that is exchanged continuously during a review session. In a preferred embodiment, the transient data may be exchanged using a technique termed user interface library (UIL), which is used to decouple user interaction from the business logic of the medical review application. When a UIL connection is established using a TCP socket connection, the MRA and XRA can communicate using a set of shared UI elements, such as the selected frame, as well as various settings concerning the display of the 3D or XR content, e.g. the threshold and transparency for volume rendering, as well as brightness and contrast for MPR planes, a pen type for editing of 3D or 4D models, and settings for regulating which objects (volume data, renderings and models) are displayed.

According to an embodiment, the XRA is configured to be used with XR hardware via an XR operating system, wherein the XR hardware in particular comprises an XR headset and XR controllers. In a preferred embodiment, the XRA is configured to be used with commercially available XR hardware, such as the HTC vive® or the Oculus Rift® VR headset and VR controllers. This XR hardware already comes with a XR operating system (driver software), and the XRA is configured to communicate with the XR operating system of the XR hardware and to process e.g. user input like head movements or XR controller interactions, and to direct the views of the 3D content generated in the XRA onto the two screens of the XR headset. This may be achieved by the XRA using a standard API (Application Programming Interface), such as Open XR, to communicate with the XR operating system. These XR/VR standards are commonly known and allow to use many different XR headsets for the extended reality-based user interface add-on. Preferably, the XR hardware comprises also two XR controllers, which can be used as 3D mouse, allowing the user to e.g. grab an object displayed in the VR environment with one hand and rotate/ tilt/move it with the other.

According to a further aspect, the invention is directed to an extended reality-based user interface add-on (XRA) configured to be operatively coupled via a data exchange channel to a medical review application having a processing module configured to process a 3D or 4D dataset to generate 3D content, wherein the extended reality-based user interface add-on is configured to interpret the 3D content received via the data exchange channel and convert it into XR content in a data format readable by an XR operating system of an XR hardware, wherein the XR hardware in particular comprises a XR headset, such that the XR hardware can display the XR content generated by the processing module; and wherein the extended reality-based user interface add-on is configured to process any user input events received from the XR operating system, in particular user input events generated using XR controllers, and to convert the user input events into user input commands readable by the medical review application, and to transfer the user input commands via the data exchange channel to the medical review application.

The XRA according to this aspect is preferably configured as explained above. It is a comparatively lean software solution that can be coupled with a number of different medical review applications allowing to review 3D or 4D datasets, as the XRA only requires the exchange of certain well-defined data. Such data exchange can be realized with a defined data interface to the MRA allowing the exchange of simplified and standardized operating actions and data via a data exchange channel. The extended reality-based user interface add-on may in particular be implemented on a computer or digital processing device, having a processing unit, a data storage and devices to allow user input and output.

According to a further embodiment, the invention is also directed to a method for analysing a 3D or 4D dataset, in particular of a human or animal organ using the system as described herein. The method comprises the following steps:

processing the 3D dataset to generate 3D content on the processing module;

optionally, the 2D graphical user interface displaying the 3D content;

the data exchange channel directing the 3D content to the extended reality-based user interface add-on and the extended reality-based user interface add-on interpreting and processing the 3D content and converting it to XR content displayable to a user by XR hardware;

receiving user input commands on one of the user interfaces;

directing the user input commands to the processing module directly from the 2D graphical user interface or via the data exchange channel from the extended reality-based user interface add-on;

the processing module processing the 3D content based on the user input commands to generate modified 3D content, directing the modified 3D content to the 2D graphical user interface and the data exchange channel;

optionally, the 2D graphical user interface displaying the modified 3D content; and the data exchange channel further directing the modified 3D content to the extended reality-based user interface add-on and the extended reality-based user interface add-on interpreting and processing the modified 3D content and converting it into modified XR content displayable to a user by XR hardware.

These steps allow a user to interact with the 3D content, for example in order to modify a model of an anatomical structure, or to take measurements, set landmarks or make annotations. This will result in a modified 3D content. According to the method of the invention, it is possible for the user to make the user input in any one of a 2D user interface or the XR user interface add-on, and to generate modified 3D content therewith. The modified 3D content will be directed to the 2D user interface and the data exchange channel, so that the user may view the modified 3D content either on the 2D user interface, or on the XR hardware. Accordingly, the invention is also directed to a workflow that require some steps being implemented on the XRA and other steps on the conventional, 2D user interface. For the steps in the XRA, the 3D dataset is rendered and the user is enabled to manipulate it and to provide input events. However, the next workflow steps may take place on the 2D user interface on the modified 3D content, based on the input provided by the user in the XRA. Thereby, it is possible to implement different steps of a workflow on the user interface that is better suited for any given step. By using the disclosed XRA, the XR content displayed by the XR hardware is always in sync with the medical review application.

According to a preferred embodiment, the method may comprise the following steps:

processing the 3D dataset to generate a rendering of a 3D dataset and a 3D model of an anatomical structure depicted by said 3D dataset;

displaying the 3D model and the rendering via the extended reality-based user interface add-on;

allowing a user to check the 3D model on the extended reality-based user interface add-on and to provide user input commands to adjust the 3D model;

the data exchange channel directing the user input commands from the extended reality-based user interface add-on to the processing module;

the processing module processing the user input to generate a modified 3D model;

directing the modified 3D model to the 2D graphical user interface, and the 2D graphical user interface displaying the modified 3D model;

optionally allowing a user to perform additional analysis and/or measurements on the modified 3D model in the 2D graphical user interface.

Therein, the user may make optimal use of the XR environment in order to check a 3D model, for example a mesh representing the mitral valve. It is also possible to try out different valve implants on the volume rendering of the mitral valve, preferably the dynamic representation thereof, in the XR environment.

According to an embodiment, the processing of the 3D dataset to generate 3D content may comprise at least one of data-compressing the 3D or 4D dataset, rendering the 3D dataset, volume rendering the 3D dataset, calculating an MPR texture of an MPR plane through the 3D dataset, segmenting the 3D or 4D dataset, generating a 3D or 4D model of an object, in particular a medical device or anatomical structure, generating a graphical primitive, and/or taking a measurement responsive to user input.

The invention is also directed to a computer program comprising program code instructions, which, when executed by a processing unit, enables the processing unit to carry out the method disclosed herein, or to implement the system according to the invention, or the extended reality-based user interface add-on, according to the invention. The method may also be carried out on several processing units. The processing unit or computational unit may be any processing unit such as a CPU (Central Processing Unit) or GPU (Graphics Processing Unit). The processing unit may be part of a computer, a cloud, a server, mobile device such as a laptop, tablet computer, mobile phone, smartphone, etc. In particular, the processing unit may be part of an ultrasound imaging system.

The invention is also directed to a tangible, non-transitory computer-readable medium that stores computer executable instructions, which, when executed by a processing unit, enable the processing unit to carry out the method according to the invention, or to implement the system or the XRA according to the invention. Such tangible, non-transitory computer-readable medium may be any digital storage medium, for example a hard disk, a server, a cloud server, an optical or a magnetic digital storage medium, a CD-ROM, an SSD-card, an SD-card, a DVD or an USB or other memory stick.

According to a further aspect, the invention is directed to a computational unit configured to implement the system according to the invention. Such computational unit may comprise a processing unit as described herein, as well as hardware to implement the 2D user interface, such as a screen and a user input device such as a mouse, touch screen, track ball, etc. The computational unit is configured to be used together with XR hardware as described herein, in particular an XR headset and XR controllers, in particular VR headset and VR controllers.

SHORT DESCRIPTION OF THE FIGURES

Useful embodiments of the invention shall now be described with reference to the attached figures. Similar elements or features are designated with the same reference signs in the figures. Different embodiments shown are explicitly allowed to be combined unless noted otherwise.

DESCRIPTION OF EMBODIMENTS

Figure 1:
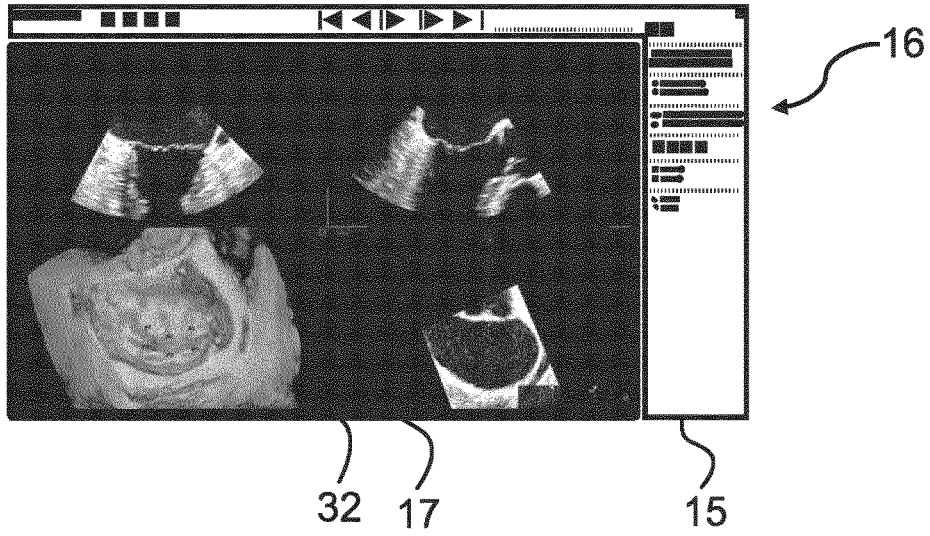
FIG. 1 shows a state of the art 2D user interface on a screen that is part of a medical review application.

FIG. 1 shows a conventional state of the art 2D user interface 16 that is part of a medical review application (MRA) 4, e.g. a TOMTEC® medical review application. In this case, the 2D user interface, comprises both a graphical user interface (GUI) 15 which enables the user to interact with the application, and a region 17 showing a 2D representation of 3D content 32 and which is termed the "diagnostic region" of the MRA 4. In the diagnostic region 17, the MRA 4 outputs a 2D representation of 3D content 32, such as the 3D volume rendering 32. The GUI 15 and the corresponding 2D representation of 3D content 32 of the diagnostic region 17 may for example be displayed on a computer monitor or on the screen of a tablet. User interaction, for example via a mouse or a trackball, which might comprise navigation or drawing of measurements, is generally handed through the diagnostic region 17 as well as the GUI 15. In an embodiment, the diagnostic region 17 is a region, possibly divided into several windows, in which the MRA 4 provides an open graphics library (open GL) context for the rendering of the 2D representation of 3D content 32. Common graphical user interface parts, like for example sliders for brightness or contrast, 3D filters and start/stop buttons for controlling the display of time-dependent medical image data, are part of the graphical user interface 15, which surrounds the diagnostic region 17 in the embodiment shown in FIG. 1.

Figure 2:
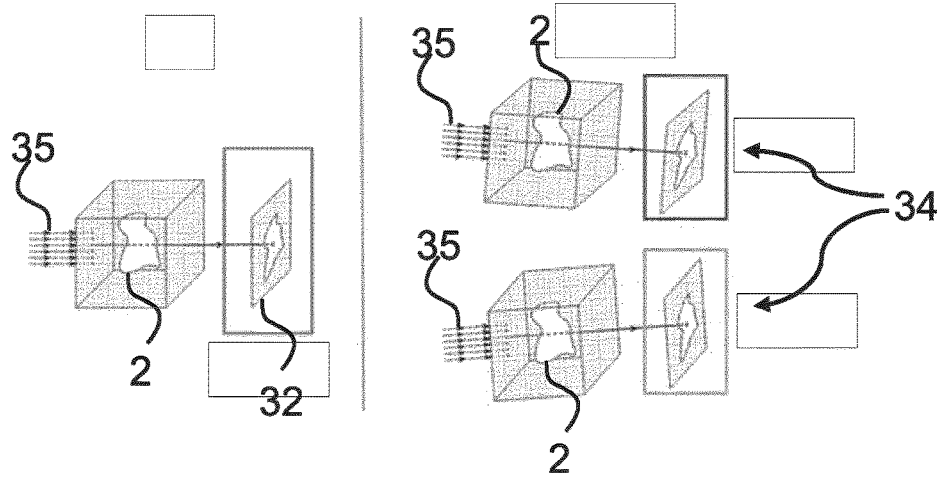
FIG. 2 shows a schematic representation of the working principle of volume rendering of 3D images.

FIG. 2 shows a schematic representation of the working principle of volume rendering of a 3D image dataset 2. Volume rendering can for example be executed in the form of direct volume rendering, in particular volume ray casting. Looking at the left side of FIG. 2, a ray 35 is generated for each image pixel of the 2D image 32 that is to be rendered. This ray is directed, i.e. cast, through the 3D image volume 2 containing 3D content. While the ray is passing through the volume, equidistant sampling points are selected. These sampling points are generally in between voxels and, therefore, the values of the sampling points are usually interpolated from the surrounding voxels. The sampling points are then shaded, i.e. coloured and lit according to their surface orientation and the location of a light source and composited along the ray of sight. This results in the final colour and/or brightness value for the processed pixel. Doing this once for every pixel of the final 2D image will result in a 2D representation of the 3D content 32, as is shown on the left side of FIG. 2. In order to obtain an XR representation of the 3D content, two different two-dimensional images 34 are rendered from slightly different perspectives, the two perspectives representing the left and the right eye of an observer. This is shown on the right side of FIG. 2. The two slightly different 2D images 34 are then projected into the left and right eye of a user respectively, thereby generating the impression of a three-dimensional object. Projecting different images into each of the user's eye can for example be realized via an XR headset, VR glasses or by using a TV screen, a computer monitor or a projector screen with a shutter or polarisation technique and corresponding shutter or polarization glasses. This is an example of how the XR-based user interface add-on may convert 3D content 2 into XR content 34 displayable by XR hardware.

Figure 3:
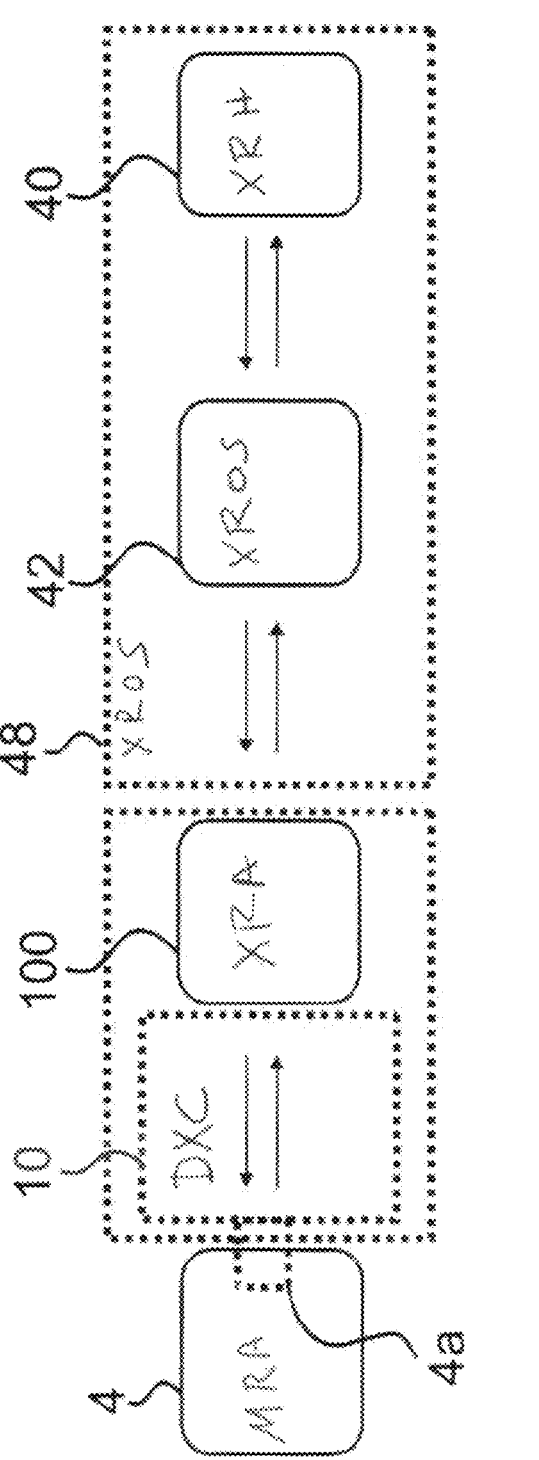
FIG. 3 shows a schematic illustration of a system according to an embodiment of the invention.

FIG. 3 shows a schematic illustration of a system according to an embodiment of the invention. A medical review application (MRA) 4 comprises a data interface 4a, through which the MRA 4 is connected to a data exchange channel 10. The data exchange channel (DXC) 10 in turn is connected to an XR-based user interface add-on (XRA) 100. Through the data interface 4a and the data exchange channel 10, the MRA 4 may send coordinates of measurement primitives and measurement values, which are generated at the MRA 4, to the XRA 100. The XRA 100 is operatively connected to an XR environment 48, in order to display XR content to a user. The XRA generates XR content from the 3D content, which the XRA 100 receives from the MRA 4 through the data exchange channel 10. The 3D content may for example comprise the coordinates of measurement primitives and measurement values, as well as 3D or 4D images. It may be displayed statically, i.e. without animation, or dynamically, i.e. in the form of an animation. In the case of a dynamic display, the XRA may apply a buffering of objects to achieve a smooth display. In order to communicate with the XR hardware 40 of the XR environment 48, the XRA 100 is configured to use the XR operating system 42 of the specific XR hardware 40, which is comparable to the driver of the XR hardware 40, and which may be commercially available. In more detail, the XRA 100 may be configured to use an application programming interface (API) or a software development kit (SDK) of the XR operating system 42. The XR operating system (XROS) 48 then sends a stereoscopic image or several stereoscopic images that represent the XR content to the XR hardware 40, in particular to an XR-based headset 44.

Optionally, the user 30 is allowed to provide user input 18 via an XR controller 46, for example by pressing or releasing a button, by moving the controller and/or by pulling a trigger, or simultaneously doing several of these interactions. This user input 18 is registered at the XR operating system 42, which is adapted to transmit coordinates and interactions of the user to the XRA 100. Hence, the user input 18 signal may for example comprise coordinates describing the position of a virtual pointer controlled by the XR controller 46, a user command like pressing a button that conveys a certain meaning, e.g. the command to take a measurement or to manipulate a 3D model, and/or the timestamp of the user's action. Editing within one frame may be carried out while data is displayed statically. It is conceivable to have a play/pause function that allows the user 30 to switch between a dynamic and a static mode. Furthermore, there might be a "previous frame"/"next frame" function to go through consecutive frames step by step. The XRA 100 is configured to process the user input 18 and direct updated information, like a 3D mouse position and interactions as well as a command to take a measurement at a certain position and time, to the MRA 4 via the data exchange channel 10 and the data interface 4a. The MRA 4 is configured to process this new information and generate an accordingly updated 3D content. This updated content will again be directed to the XRA 100 via the data interface 4a and the data exchange channel 10, converted to XR content by the XRA 100, and be presented to the user via the XR environment 48 in the same manner as described before.

Advantageously, the user input commands comprising the user input 18 that are submitted via the XRA are very basic and comparable to the commands a user would submit via a computer mouse to a computer. By integrating common APIs like OpenXR, the XRA 100 can communicate with a wide range of existing XR hardware (XRH) 40 through the hardware's operating system 42. Here, the XRA 100, on the one hand, prepares the 3D content to be presented to a user 30 as XR content via the XR environment 48 and, on the other hand, provides the means to "translate" user input 18 via the XR hardware 40 into a language that can be understood and transmitted by the data exchange channel 10. Because all the commands submitted this way are very simple and no processing of data other than preparing it for display to a user 30 is carried out, the XRA 100 itself may remain very simple. Through the use of a very universal language of communication by the data interface 4a and the data exchange channel 10 that is compatible with many already existing MRAs 4, the XRA 100 can be used to provide an XR environment 48 for many different MRAs 4. The XRA 100 thereby updates the MRAs 4 to not only have a 2D user interface but an additional XR user interface as well. By utilizing commonly available XR hardware 40, the XRA thus provides an easily obtainable and comparatively low-priced way of upgrading existing medical reviewing systems.

Figure 4:
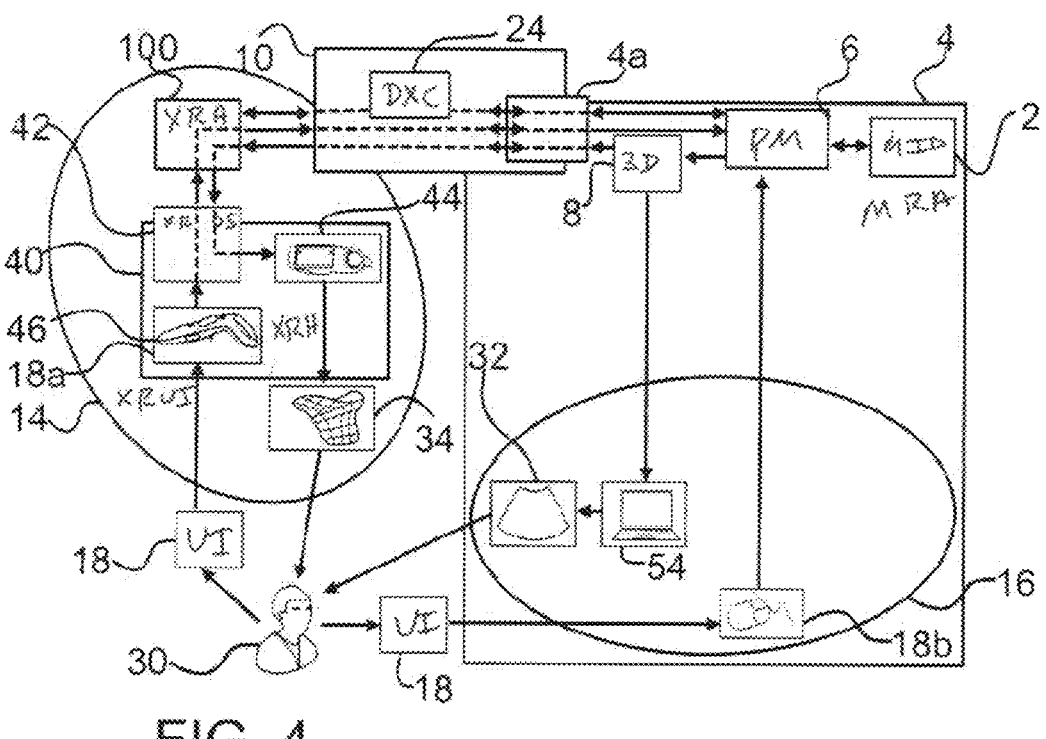
FIG. 4 shows a schematic representation of a system for reviewing 3D or 4D medical image data according to an embodiment of the invention.

FIG. 4 shows a schematic representation of a system for reviewing 3D or 4D medical image data (MID) 2 according to an embodiment of the invention. The system comprises a processing module (PM) 6 of an MRA 4, which is configured to process 3D or 4D medical image data 2, which may be uploaded from a digital storage medium, in order to generate 3D content 8. This 3D content 8 is then transferred to a 2D user interface 16 that displays the 3D content 8 on a 2D screen 54, for example a computer monitor or a tablet screen, in the form of a 2D representation of 3D content 32. This 2D representation of 3D content 32 may be observed and analysed by a user 30, who may provide user input 18 via a user input device of the graphical user interface (GUI) 18b. The user input 18 is then directed to the processing module 6, which processes the user input (UI) 18. The processing module 6 and the 2D user interface 16 are part of an MRA 4. Such an MRA 4 alone is known from the state of the art.

However, the system according to the invention furthermore comprises a data exchange channel 10 that is operatively coupled to the processing module 6 via a data interface 4a and configured to interface the processing module with an additional user interface 14. In the embodiment shown in FIG. 4, the data exchange channel 10 is operatively coupled to an XRA 100, which in turn is coupled to an XR operating system 42. User interface elements 24 of the MRA 4 and of the XRA 100 are continuously synchronized via the data exchange channel 10. By utilizing the XR operating system 42, the XRA 100 is coupled to XR hardware 40 comprising an XR headset 44 and an XR controller 46. The data exchange channel 10 is adapted to direct 3D content 8 generated by the processing module 6 to the XRA 100, which in turn directs the 3D content 8 in the form of XR content via the XR operating system 42 to the XR headset 44. Finally, the XR headset 44 displays a 3D representation of the 3D content 34 to the user 30. The displayed content may comprise for example static or dynamic textures on a surface model and/or values for a measurement.

Advantageously, such a stereoscopic view may give the user 30 a better grasp of complex 3D environments and may even unveil a level of detail hardly possible in a 2D user interface 12. Furthermore, a 3D representation of 3D content 34, i.e. of clinical data, is closer to a surgeon's view thus decreasing the gap between clinical procedure and analysis. Additionally, as an XR view is in many cases more intuitive and less abstract it may advantageously be used in various training and educational contexts, as well as for helping to explain medical conditions to a patient through visualization.

The user 30 is enabled to generate user input 18 via a user input device of the XR-based user interface 18a, which in this case is an XR controller 46. It is also conceivable that the user 30 may use more than one controller, e.g. one XR controller 46 in each hand. Each controller may have a different task. For example, one controller might be dedicated to an actual measurement, while the other controller is used to hold and navigate MPR-planes and surface models. Alternatively, one controller might be used for rotating a whole scene, while the other one is used for rotating the view around a fixed axis. In the case of any such user input 18, the system is configured to direct the user input 18 via the XR operating system 42, the XRA 100, the data exchange channel 10 and the data interface 4a to the processing module 6, which in turn is configured to process the user input 18. Thereby, because XR utilizes the human eye-hand coordination far more than mouse-based or trackball-based approaches, a more intuitive navigation in medical 3D or 4D medical image data 2 is made possible. This allows for more efficient and effective measurements and/or more direct input commands. Furthermore, it is also conceivable that the user 30 can switch between different measurement visualizations or between different datasets. This may be realized in connection with saving and loading bookmarks. e.g. of UI elements or other settings and/or states of data analysis.

Additionally, it is conceivable that a presenter being an active user 30, e.g., a presenter in a lecture on a congress, executes a workflow in an XR environment 48 while several passive observers can watch using their own XR hardware 40. Alternatively, the role of the active user 30 may be switched during a medical discussion among two colleagues, e.g. among two physicians.

The XR operating system 42 can also be seen as a driver software for the XR hardware 40 that is incorporated in or used by the XRA 100 to communicate with an XR hardware 40, i.e. with the XR headset 44 and the XR controller 46. Advantageously, the XR operating system 42 can be an application programming interface (API) such as e.g. OpenXR, which supports various different XR hardware devices. The system is adapted to allow the user 30 to switch between the XR-based user interface (XRUI) 14 and the 2D user interface 16 of the MRA at any time. Therefore, the user 40 can, for example, look at a 2D representation of 3D content 32 at the 2D screen 45 of the 2D user interface 16 in order to get an overview of the medical data, e.g. of an organ, and then switch to the XR-based user interface 14, in order to have a more detailed and possibly more intuitive look at the 3D content 8 via the 3D representation of the 3D content 34. Next, the user 30 may issue user input commands 18 at the XR-based user interface 14 via the XR controllers 46, for example to rotate the image or take some measurements. Afterwards the user 30 may switch back to the 2D user interface 16 of the MRA 4 to have a 2D look at changes of the 3D content 8 issued by the processing module 6 due to the previous user input 18 at the XR-based user interface 14. The user 30 may then revise the 3D content 8 and possibly apply further changes via the user input device 25 of the graphical user interface 18b.

Figure 5:
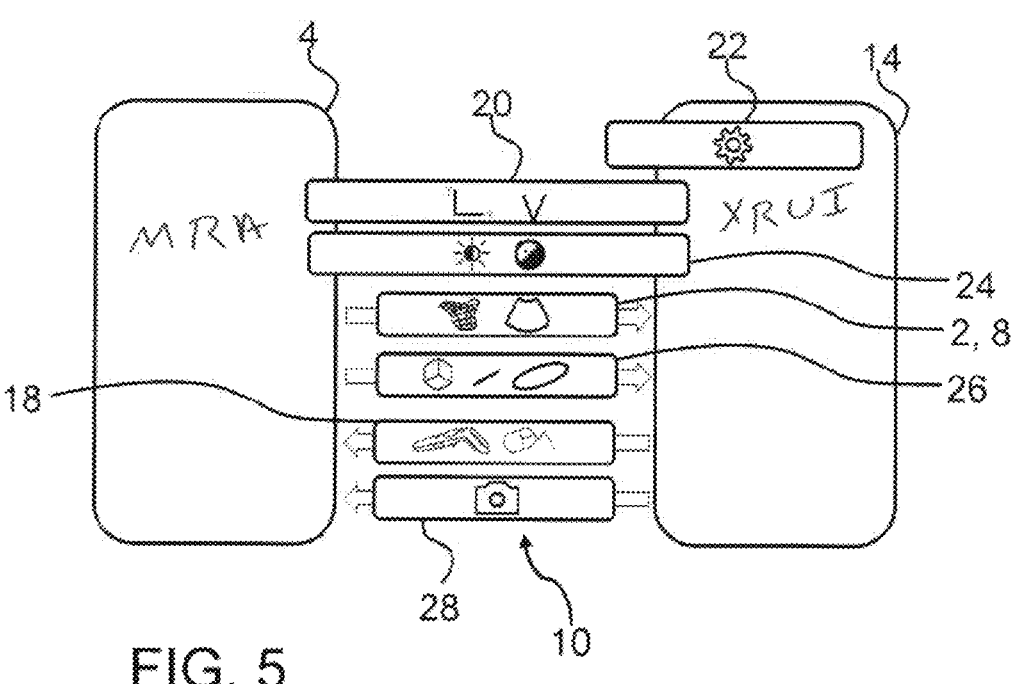
FIG. 5 shows a schematic illustration of the operational connection between the medical review application and the XR-based user interface via the data exchange channel according to an embodiment of the invention.

FIG. 5 shows a schematic illustration of the operational connection between the MRA 4 and the XR-based user interface 14 via the data exchange channel 10 according to an embodiment of the invention. In this embodiment, the MRA 4 and the XR-based user interface 14 share a temporal and spatial reference system 20 through the data exchange channel 10. This temporal and spatial reference system 20 is preferably exchanged during the initial connection between the MRA 4 and the XR-based user interface 14, when establishing a review session ("initial handshake"). For example, it allows the conversion between volume frames and times and defines phase loops and time stamps. A phase loop may be understood as a temporal region within the complete 3D dataset, for which 3D measures or segmentations are created. While the 3D data may comprise several heart cycles, it is beneficial in some cases to create 3D measurements or segmentations of only one cycle or of only a part of one cycle that is most interesting for the analysis of the heart or of a part of the heart, such as a mitral valve. A dynamic display of such a phase loop comprises animating over the phase loop. In this embodiment, these phase loops, and in particular the range of those phase loops, as well as time stamps within such phase loops, are synchronized between the MRA 4 and the XR-based user interface 14.

Furthermore in this embodiment, the MRA 4 and the XR-based user interface 14 share a common coordinate system 20 via the data exchange channel 10. It serves as reference system, for example to position 3D objects in relation to the 3D volume. Furthermore, the XR-based user interface 14 comprises configuration settings 22 that are used during an established session with an MRA 4. The configuration settings may comprise a unique application identifier, such as an application name and an application version, special start options, an exchange configuration (e.g. an IP address, a port and/or exchange folders), a protocol configuration (e.g. a protocol version and/or allowed types of commands), a UI configuration and style options for data objects (e.g. line width and colour). These configuration settings 22 allow the XR-based user interface 14 to communicate via the data exchange channel with an MRA 4 in order to receive and display 3D content 8, such as 3D or 4D medical image data 2, a 3D or 4D model, or 3D primitives 26 from the MRA 4 through the data exchange channel 10. The configuration settings 22 may further allow the XR-based user interface 14 to be used with more than one different MRA 4, and to adapt to the properties of each of the different MRAs 4. The configuration settings 22 may either be stored on the XR-based user interface 14 permanently or they may be transferred via the data exchange channel 10 during the initial handshake when initiating a session between the XR-based user interface 14 and an MRA 4. Furthermore, it is provided that the MRA 4 and the XR-based user interface 14 share user interface elements 24, which are continuously synchronized via the data exchange channel 10. The user interface elements 24 comprise a value of a user interface element, an identifier of a selected frame of the 3D or 4D medical image data 2, settings concerning the display of the 3D content 8 such as a threshold or transparency for volume rendering or brightness and contrast for multiplanar reconstruction planes, and/or a 3D mouse position.

During a session, 3D content 8 is directed from the MRA 4 via the data exchange channel 10 to the XR-based user interface 14. The 3D content is typically generated by the processing module 6 and may comprise rendering of the 3D or 4D medical image data 2, a particular frame of a 4D dataset, an MPR texture generated from the 3D or 4D medical image dataset, a 3D or 4D model of an object and/or a mesh. Furthermore, 3D primitives 26, a text of an annotation and/or a number indicating a measurement may be transferred. In principle, it might be also conceivable to transfer the 3D or 4D medical image dataset directly via the data exchange channel to the XR-based user interface 14 and render it at the XR-based user interface 14. This necessitates rendering capabilities of the XR-based user interface 14, but on the other hand has the advantage that the total data transfer between the MRA 4 and the XR-based user interface 14 is lower.

User input 18 at the XR-based user interface 14 is directed to the MRA 4, in particular to the processing module 6, via the data exchange channel 10. Preferably, the input is issued with a user input device of the XR-based user interface 18a, e.g. an XR controller 46, but it might be also conceivable to use other input devices such as a computer mouse or keyboard. Furthermore, also a prompt to take a screenshot 28 may be issued at the XR-based user interface 14, which will be stored at the MRA 4 in order to review or print it later.

In summary, the XR-based user interface 14 may be configured to issue only very basic commands via the data exchange channel 10 in combination with configuration settings 22, which allow for the XR-based user interface 14 to be used with different MRAs 4. The XR-based user interface 14 thus provides a very versatile, yet also simple solution to upgrade already existing MRAs 4 with comparatively low effort and expenses.

Figure 6:
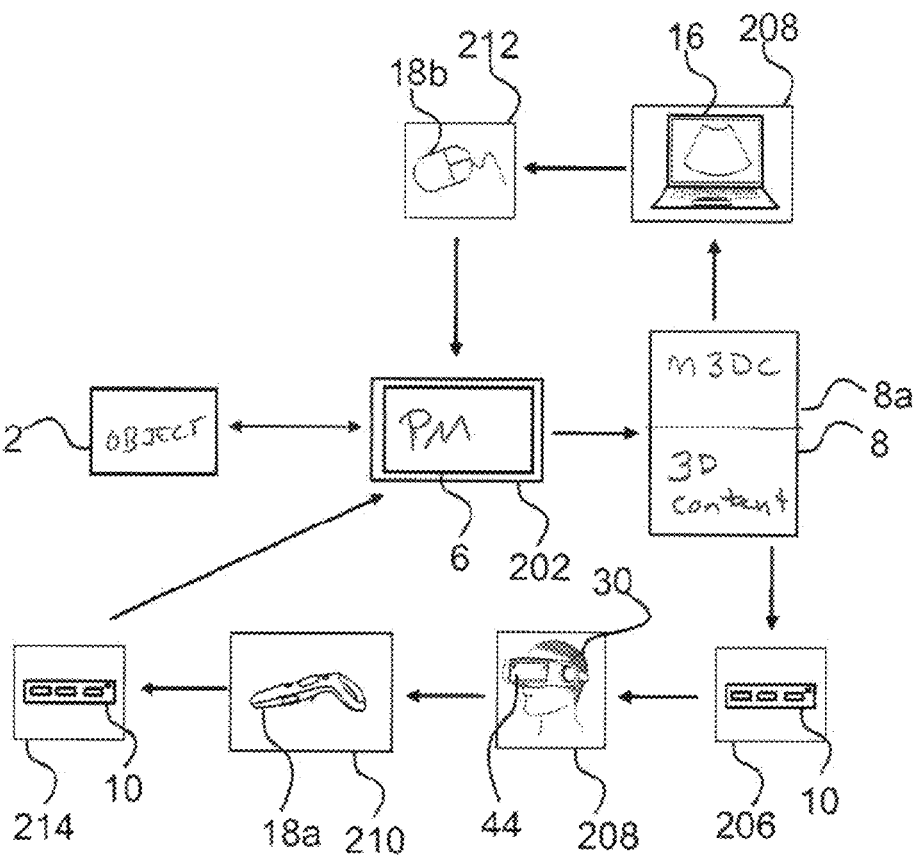
FIG. 6 shows a flow diagram of a method for analysing a 3D or 4D dataset according to an embodiment of the invention.

FIG. 6 shows a schematic illustration of a method for analysing a 3D or 4D dataset 2 according to an embodiment of the invention. The method comprises a step of processing the 3D or 4D dataset 2 on the processing module 6, in order to generate 3D content 8. This 3D content 8 is then directed to the 2D user interface 16 and/or to the data exchange channel 10, which in turn directs the 3D content to the XR-based user interface 14. As a next step, the 3D content is then displayed on the XR-based user interface 14 and/or on the 2D user interface 16 of the MRA 4. This enables a user 30 to look at a 3D representation of 3D content 34 (referred to as XR content) or at a 2D representation of 3D content 32, alternatively or successively. The user has then the option to issue user input 18 either on the XR-based user interface 14 or on the 2D user interface 16. User input 18 at the 2D user interface 16 will be directed to the processing module 6 directly, while user input at the XR-based user interface 14 will be directed to the processing module 6 via the data exchange channel 10. The processing module 6 will process the 3D content 8 based on the user input 18 and thereby generate modified 3D content 8a. This modified 3D content (M3DC) 8a is directed to the 2D user interface 16 and displayed at the 2D user interface 16 and/or directed to the data exchange channel 10, which further directs the modified 3D content 8a to the XR-based user interface 14 which also displays the modified 3D content 8a. Optionally, the user 30 might again issue a user input 18 at either of the user interfaces 14, 18 which will be directed either directly or indirectly via the data exchange channel 10, respectively, to the processing module for processing. Accordingly, this cycle might be repeated as many times as it is necessary or useful for the user 30 to achieve a desired result, in particular to complete a workflow of reviewing medical image data.

Figure 7:
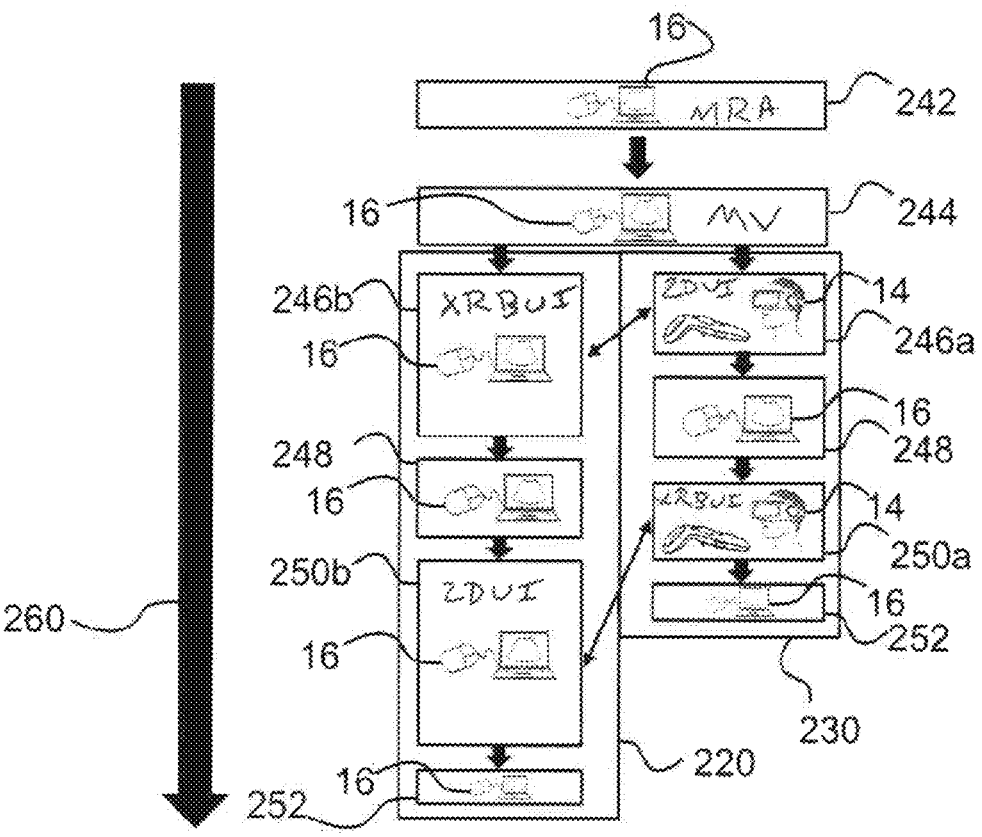
FIG. 7 shows a flow diagram of a method according to another specific embodiment of the invention in comparison with a conventional method having the same purpose.

FIG. 7 shows a schematic illustration of a method according to another specific embodiment of the invention (right side) in comparison with a conventional method (left side) having the same purpose. The workflow steps are shown one below the other, with the height of each step indicating the amount of time (illustrated by arrow 260) required for each step. In particular, a specific medical workflow for analysing a pathologic mitral valve is shown, which is used to decide which bioprosthetic valve size fits best as an implant that will be implanted at a surgical intervention. As a first step, the 3D dataset is loaded into the MRA 242. Following this first step, initial landmarks are placed for the segmentation of a mitral valve (MV) 244 on the 2D user interface 16 of the MRA 4. After the second step, the workflow according to this embodiment of the invention 230 differs from the conventional workflow 220. In the conventional workflow 220, the third step is to check and adjust the segmentation on the 2D user interface (2DUI) 246b, in particular, on a 2D screen 54, with mouse and keyboard. For the workflow with the XRA 230, the third step is to check and adjust the segmentation on the XR-based user interface (XRBUI) 246a. As tests have shown, the time needed for the third step in the workflow with the XRA 230 is significantly lower than for the corresponding step in the conventional workflow 220. The following, fourth step is identical in both workflows and consists of analysing the resulting MV parameters and selecting a correct device size 248. In both cases this workflow step is carried out on the 2D user interface 16. Accordingly, the same amount of time is needed for these four steps in both workflows. The fifth workflow step differs again in that in the conventional workflow 220 additional measurements are performed and/or the device position is checked and adjusted on the 2D user interface (2DUI) 250b, while in the workflow with the XRA 230, additional measurements are performed and/or the device position is checked and adjusted on the XR-based user interface (XR-BUI) 250a. Again, it has been shown that significantly more time is needed for the conventional workflow step than for the corresponding workflow step with the XRA 230. When the analysis is finished, in the final step 252 a larger amount of time 260 has passed in the conventional workflow 220 than in the workflow with XRA 230.

In addition to the workflow steps described above, further workflows with further workflow steps are conceivable, such as 4D analysis and/or assessment of the function of the left and right ventricle or of the mitral valve via surface models, 4D cardio views for volume measurements via surface models, or analysis of 4D radiological ultrasound data, e.g. TomTec® SONO-SCAN. It has turned out that the workflow steps in an XR environment 48 are not only more efficient, i.e. faster, than conventional 2D workflow steps, but they are also more effective and reliable by leading to a lower variability in measurement results. Furthermore, due to the more intuitive approach, a lower training time of new users 30, e.g. physicians, is to be expected.

Figure 8:
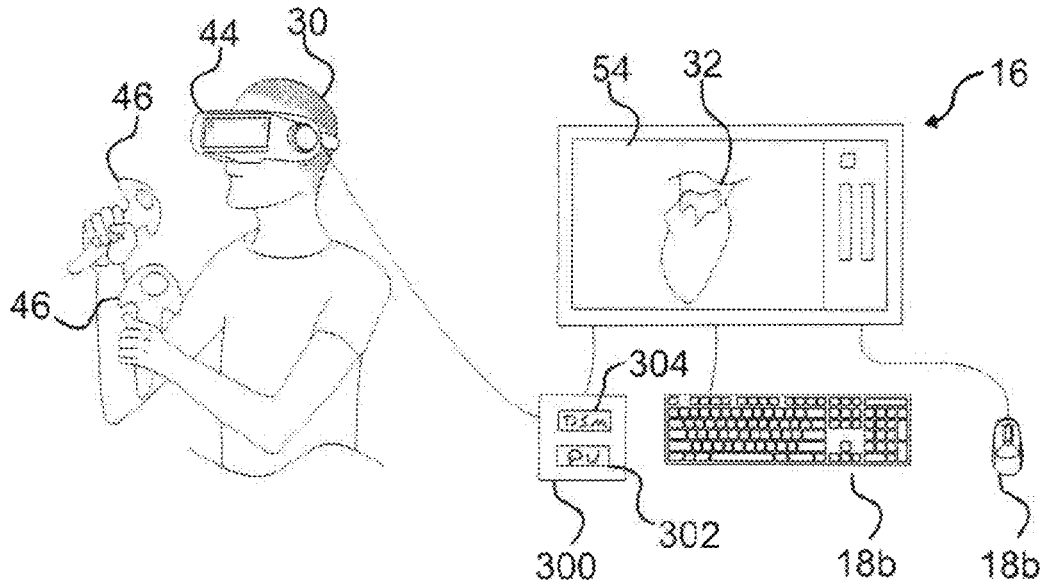
FIG. 8 shows a schematic view of the implementation of a system according to the invention on a computer with corresponding hardware.

FIG. 8 shows a schematic illustration of the implementation of a system according to the invention on a computer 300 with corresponding hardware. The computer may comprise a processing unit (PU) 302 and a digital storage medium (DSM) 304, on which the system is installed as software product. The XR hardware 40, comprising XR controllers 46 and an XR headset 44, is connected to the computer, on which the XR-based user interface 100 is installed. At the same time an MRA 4 is also installed on the computer 300 and connected to hardware comprising user input devices of the 2D user interface 18b and a 2D screen 54. A 2D representation of 3D content 32 is displayed on the screen 54. The user may switch between the XRA 100 and the 2D user interface 16 at any time.

Figure 9:
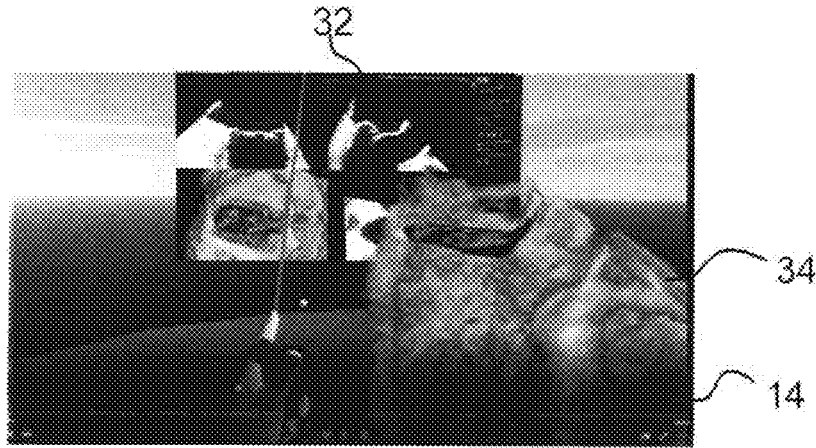
FIG. 9 shows a view from the perspective of a user when using the XR-based user interface according to an embodiment of the invention.

FIG. 9 shows a view from the perspective of a user 30 when using the XR-based user interface 14 according to an embodiment of the invention. In this embodiment, the user 30 can see both a 2D representation of 3D content 32 and a 3D representation of 3D content 34 at the same time in the XR-based user interface 14. For example, a user 30 might rotate a 3D model and thereby create new slices in a multi planar reconstruction. On the other hand, it is also conceivable to have different visualizations, e.g. of a model of a mitral valve, such as a wireframe model, a cutline with a plane and/or a cutline and a transparent (ghost) model in the XR environment.

The above discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present invention, as set forth in the claims that follow. Accordingly, the specification and drawings are to be regarded as an illustrative manner are not intended to limit the scope of the appended claims.

REFERENCE SIGNS

1 system
2 3D or 4D medical image data/dataset
4 medical review application (MRA)
4a data interface
6 processing module
8 3D content
8a modified 3D content
9 3D models
10 data exchange channel
12 user interface
14 XR-based user interface
15 Graphical user interface
16 2D user interface
17 Diagnostic Region
18 user input
18a user input device of the XR-based UI 18*b* user input device of the 2D user interface
20 temporal and spatial reference system
22 configuration settings
24 UI elements
26 3D/graphical primitives
28 screenshots
30 user
32 2D representation of 3D content
34 XR representation of 3D content
35 Ray
40 XR hardware
42 XR operating system
44 XR headset
46 XR controller
48 XR environment
54 2D screen
100 XR-based user interface add-on (XRA)
200 method
202 processing the 3D dataset
204 generate 3D content
206 directing the 3D content
208 display 3D content
210 receiving first user input commands
212 receiving second user input commands
214 directing first user input commands to the processing module
216 directing second user input commands to the processing module
220 conventional workflow
230 workflow with XRA
242 loading 3D dataset into MRA
244 placing initial landmarks for the segmentation of a mitral valve (MV)
246*a* checking and adjusting the segmentation on the XR-based user interface
246*b* checking and adjusting the segmentation on the 2D user interface
248 analysing resulting MV parameters & selecting correct device size
250*a* performing additional measurements and/or checking and adjusting the device position on the XR-based user interface
250*b* performing additional measurements and/or checking and adjusting the device position on the 2D user interface
252 finishing the analysis
260 time axis of the workflow
300 computer
302 processing unit
304 digital storage medium

The invention claimed is:

1. A system for reviewing three-dimensional (3D), or four-dimensional (4D) medical image data, having a processing unit, a data storage and devices to allow user input and output, and having an extended reality environment, the system comprising:

a medical review application comprising a processing module configured to process a 3D or 4D dataset to generate 3D content, and a 2D user interface, wherein the 2D user interface is configured to display the 3D content generated by the processing module and to allow a user to generate user input commands;

an extended reality(XR)-based user interface add-on; and a data exchange channel operatively coupled to the processing module, the data exchange channel being configured to interface the processing module with the extended reality, i.e. XR-based user interface add-on;

wherein the data exchange channel is adapted to direct the 3D content generated by the processing module to the extended reality-based user interface add-on;

wherein the extended reality-based user interface add-on is configured to interpret and process the 3D content and convert it to XR content displayable to the user in an extended reality environment;

wherein the extended reality environment is configured to allow a user to generate user input events, and the extended reality-based user interface add-on is configured to process the user input events and convert them to user input commands readable by the medical review application;

wherein the data exchange channel is adapted to direct user input commands from the extended reality-based user interface add-on to the medical review application; and wherein the processing module processes the 3D content based on the user input commands to generate modified 3D content; and wherein, responsive to a switch user interface command generated by a currently-active user interface among the extended reality-based user interface add-on and the 2D user interface, the processing module is adapted to stop responding to the user input commands from said user interface and to start responding to user input commands from the other user interface.

2. The system according to claim 1, wherein the medical review application comprises a data interface for the extended reality-based user interface add-on, wherein the data interface is operatively coupled to the data exchange channel, and is configured to allow the exchange of simplified and standardized operating actions and data between the medical review application and the extended reality-based user interface add-on.

3. The system according to claim 1, wherein the medical review application comprises a data interface for the XR-based user interface add-on, wherein the data interface is adapted to continuously synchronize corresponding user interface elements between the extended reality-based user interface add-on and the medical review application through the data exchange channel, wherein corresponding user interface elements comprise at least one of a value of a user interface element, an identifier of a selected frame of the 4D dataset, settings concerning the display of the 3D and/or XR content, and/or a 3D mouse position.

4. The system according to claim 1, wherein the XR-based user interface add-on is stateless, in that it does not have a memory of user input commands transferred to the processing module through the data exchange channel.

5. The system according to claim 1, wherein the 3D content generated by the processing module comprises a rendering of the 3D or 4D dataset, wherein the extended reality-based user interface add-on is configured to distort in perspective the rendered 3D content based on at least some of the user input and/or a user's current viewing perspective.

6. The system according to claim 1, wherein the 3D content generated by the processing module comprises at least one of an updated or data-compressed version of the 3D or 4D dataset, a rendering of the 3D or 4D dataset, a multi planar reconstruction, i.e. MPR, texture generated from the 3D or 4D dataset, a graphical primitive, a 3D or 4D model of an object, a mesh, a text of an annotation, and/or a number indicating a measurement.

7. The system according to claim 1, wherein the processing module is adapted to transfer a temporal and spatial reference system and at least one of the 3D or 4D dataset, an updated 3D or 4D dataset, a user interface element and/or configuration settings to the extended reality-based user interface add-on during establishment of a connection between the processing module and the extended reality-based user interface add-on.

8. The system according to claim 1, wherein the extended reality-based user interface add-on is adapted to transfer at least one of a 3D mouse position, a position and orientation of a multi planar reconstruction, i.e. MPR, plane, a screenshot, and/or a modified value of a user interface element, through the data exchange channel to the processing module during a connection between the processing module and the extended reality-based user interface add-on.

9. The system of claim 1, wherein the extended reality-based user interface add-on is configured to be used with XR hardware via an XR operating system, wherein the XR hardware comprises an XR headset and XR controllers.

10. A tangible, non-transitorty computer readable medium adapted to store an extended reality-based user interface add-on configured to be operatively coupled via a data exchange channel to a medical review application having a 2D user interface and a processing module configured to process a 3D or 4D dataset to generate 3D content, wherein the extended reality-based user interface add-on is configured to interpret the 3D content received from the processing module via the data exchange channel and convert it into XR content in a data format readable by an XR operating system of an XR hardware, wherein the XR hardware comprises an XR headset and XR controllers, such that the XR hardware can display the XR content generated by the processing module;

wherein the extended reality-based user interface add-on is configured to process any user input events generated using the XR controllers, and to convert the user input events into user input commands readable by the medical review application, and to transfer the user input commands via the data exchange channel to the medical review application;

wherein the processing module processes the 3D content based on the user input commands to generate modified 3D content; and wherein, responsive to a switch user interface command generated by a currently-active user interface among the extended reality-based user interface add-on and the 2D user interface, the processing module is adapted to stop responding to the user input commands from said user interface and to start responding to user input commands from the other user interface.

11. A method for analysing a 3D or 4D dataset using a medical review application comprising a processing module and a 2D user interface, a data exchange channel operatively coupled to the processing module, wherein the data exchange channel is configured to interface the processing module with an extended reality-based user interface add-on, the method comprising:

processing the 3D dataset to generate 3D content on the processing module;

optionally, the 2D user interface displaying the 3D content;

the data exchange channel directing the 3D content to the extended reality-based user interface add-on and the extended reality-based user interface add-on interpreting and processing the 3D content and converting it to XR content displayable to a user by XR hardware;

receiving user input on one of the user interfaces;

directing user input commands to the processing module directly from the 2D user interface or via the data exchange channel from the extended reality-based user interface add-on;

the processing module processing the 3D content based on the user input commands to generate modified 3D content, directing the modified 3D content to the data exchange channel and optionally to the 2D user interface;

optionally, the 2D user interface displaying the modified 3D content; and the data exchange channel further directing the modified 3D content to the extended reality-based user interface add-on and the extended reality-based user interface add-on interpreting and processing the modified 3D content and converting it into modified XR content displayable to a user by XR hardware, wherein, responsive to a switch user interface command generated by a currently-active user interface among the extended reality-based user interface add-on and the 2D user interface, stop responding to the user input commands from said user interface and to start responding to user input commands from the other user interface.

12. The method according to claim 11, the method comprising:

processing the 3D dataset to generate a rendering of the 3D dataset to provide a 3D model of an anatomical structure depicted by said 3D dataset;

displaying the 3D model and the rendering via the extended reality-based user interface add-on;

allowing a user to check the 3D model on the extended reality-based user interface add-on and to provide user input to adjust the 3D model;

the data exchange channel directing the user input commands from the extended reality-based user interface add-on to the processing module;

the processing module processing the user input commands to generate a modified 3D model;

directing the modified 3D model to the 2D user interface, and the 2D user interface displaying the modified 3D model; and optionally allowing a user to perform additional analysis and/or measurements on the modified 3D model in the 2D user interface.

13. The method according to claim 11, wherein the processing module is configured to process the 3D or 4D dataset and generate 3D content and/or XR content by at least one of data-compressing the 3D or 4D dataset, rendering the 3D dataset, volume rendering the 3D dataset, calculating a multi planar reconstruction, i.e. MPR, texture of an MPR plane through the 3D dataset, segmenting the 3D or 4D dataset, generating a 3D or 4D model of an object, generating a graphical primitive, and/or to taking a measurement responsive to user input.

14. A tangible, non-transitory computer readable medium that stores program code instructions which, when executed by a processing unit, cause the processing unit to:

process a 3D dataset to generate 3D content;

optionally, cause a 2D user interface to display the 3D content;

receive user input commands directly from the 2D user interface or via a data exchange channel from an extended reality-based user interface add-on, wherein the data exchange channel is configured to direct the 3D content to the extended reality-based user interface add-on, and wherein the extended reality-based user interface add-on is configured to interpret and process the 3D content and convert it to XR content displayable to a user by XR hardware;

process the 3D content based on the user input commands to generate modified 3D content;

direct the modified 3D content to the data exchange channel and optionally to the 2D user interface;

optionally, cause the 2D user interface to display the modified 3D content;

cause the data exchange channel to further direct the modified 3D content to the extended reality-based user interface add-on;

cause the extended reality-based user interface add-on to interpret and process the modified 3D content and to convert it into modified XR content displayable to a user by XR hardware;

based on the user input commands to generate modified 3D content; and responsive to a switch user interface command generated by a currently-active user interface among the extended reality-based user interface add-on and the 2D user interface, stop responding to the user input commands from said user interface and start responding to user input commands from the other user interface.

15. The tangible, non-transitory computer readable medium according to claim 14, wherein the medical review application comprises a data interface for the extended reality-based user interface add-on, wherein the data interface is operatively coupled to the data exchange channel, and is configured to allow the exchange of simplified and standardized operating actions, and data between the medical review application and the extended reality-based user interface add-on.

16. The tangible, non-transitory computer readable medium according to claim 14, wherein the medical review application comprises a data interface for the XR-based user interface add-on, wherein the data interface is adapted to continuously synchronize corresponding user interface elements between the extended reality-based user interface add-on and the medical review application through the data exchange channel, wherein corresponding user interface elements comprise at least one of a value of a user interface element, an identifier of a selected frame of the 4D dataset, settings concerning the display of the 3D and/or XR content, and/or a 3D mouse position.

17. The tangible, non-transitory computer readable medium according to claim 14, wherein the XR-based user interface add-on is stateless, and does not comprise a memory of user input commands transferred to the processing module through the data exchange channel.

18. The tangible, non-transitory computer readable medium according to claim 14, wherein the 3D content generated by the processing module comprises a rendering of the 3D or 4D dataset, wherein the extended reality-based user interface add-on is configured to distort in perspective, the rendered 3D content based on at least some of the user input and/or a user's current viewing perspective.

* * * * *